(12) United States Patent
Yamaki et al.

(10) Patent No.: US 11,806,412 B2
(45) Date of Patent: Nov. 7, 2023

(54) OIL-IN-WATER EMULSION SUNSCREEN COSMETIC

(71) Applicant: SHISEIDO COMPANY, LTD., Tokyo (JP)

(72) Inventors: Satoshi Yamaki, Yokohama (JP); Kazutaka Sasaki, Yokohama (JP); Takashi Matsui, Yokohama (JP); Kazuhiro Yamaguchi, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 15/521,490

(22) PCT Filed: Oct. 30, 2015

(86) PCT No.: PCT/JP2015/080765
§ 371 (c)(1),
(2) Date: Apr. 24, 2017

(87) PCT Pub. No.: WO2016/068299
PCT Pub. Date: May 6, 2016

(65) Prior Publication Data
US 2018/0271755 A1    Sep. 27, 2018

(30) Foreign Application Priority Data

Oct. 31, 2014 (JP) ................................. 2014-222963
Sep. 15, 2015 (JP) ................................. 2015-181984

(51) Int. Cl.
| | |
|---|---|
| A61K 8/06 | (2006.01) |
| A61K 8/36 | (2006.01) |
| A61K 8/86 | (2006.01) |
| A61K 8/31 | (2006.01) |
| A61Q 17/04 | (2006.01) |
| A61K 8/37 | (2006.01) |
| A61K 8/44 | (2006.01) |
| A61K 8/40 | (2006.01) |

(52) U.S. Cl.
CPC ............... *A61K 8/062* (2013.01); *A61K 8/06* (2013.01); *A61K 8/36* (2013.01); *A61K 8/361* (2013.01); *A61K 8/37* (2013.01); *A61K 8/40* (2013.01); *A61K 8/44* (2013.01); *A61K 8/86* (2013.01); *A61Q 17/04* (2013.01); *A61K 2800/522* (2013.01)

(58) Field of Classification Search
None
See application file for complete search history.

(56) References Cited

U.S. PATENT DOCUMENTS

| | | | | |
|---|---|---|---|---|
| 7,674,472 B2* | 3/2010 | Belmar | ................... | A61K 8/361 424/401 |
| 9,066,860 B2* | 6/2015 | Nagare | .................... | A61K 8/06 |
| 2003/0180335 A1* | 9/2003 | Ohmori | ................... | A61Q 19/00 424/401 |
| 2004/0197361 A1* | 10/2004 | Oguchi | ................... | A61P 17/00 424/401 |
| 2005/0048009 A1 | 3/2005 | Goppel et al. | | |
| 2011/0206627 A1* | 8/2011 | Takakura | ................. | A61K 8/86 424/59 |
| 2013/0011348 A1 | 1/2013 | Takahura | | |
| 2014/0030298 A1 | 1/2014 | Harada et al. | | |
| 2014/0255323 A1 | 9/2014 | Ishida et al. | | |

FOREIGN PATENT DOCUMENTS

| | | |
|---|---|---|
| CN | 102740825 | 10/2012 |
| JP | H8-217619 | 8/1996 |
| JP | 8-310941 | 11/1996 |
| JP | 08310941 A * | 11/1996 |
| JP | H1-180237 | 3/1999 |
| JP | 2004-83541 | 3/2004 |
| JP | 2004-91377 | 3/2004 |
| JP | 2004-168913 | 6/2004 |
| JP | 2005-513094 | 5/2005 |

(Continued)

OTHER PUBLICATIONS

Schülke (http://www.schuelke.ru/static/html/docs/Personal%20Care%20Folder_GB.pdf), no date, p. 1-16 with a date for the cited Sensiva SC50 of at least 2001 as evidenced by industrial chemicals (https://www.industrialchemicals.gov.au/sites/default/files/NA966%20Public%20Report%20PDF.pdf ) (Year: 2001).*

Industrial chemicals, Australia "Sensiva SC50" (https://www.industrialchemicals.gov.au/sites/default/files/NA966%20Public%20Report%20PDF.pdf ) p. 1-28 (Year: 2001).*

JP1996310941/JPH08310941, jplatpat machine english translation, 1996.*

PCT/JP2015/080765, Search Report dated Feb. 2, 2016, 2 pages English, 2 pages—Japanese.

(Continued)

*Primary Examiner* — Erin E Hirt
(74) *Attorney, Agent, or Firm* — Andrew F Young; Nolte Lackenbach Siegel (57) ABSTRACT

An oil-in-water emulsified sunblock cosmetic has excellent feeling when used and maintains a high ultraviolet-ray protective effect even upon contact with water or sweat. The oil-in-water emulsified sunblock cosmetic contains an (A) ultraviolet-ray protective agent and a (B) fatty acid forming a solid at room temperature, the cosmetic is characterized in that 51% or less of the fatty acid is neutralized, and the formulation ratio ((A)/(B) of the (A) ultraviolet-ray protective agent to the (B) fatty acid is in the range of at least 0.1 and less than 10.0. The cosmetic exhibits the unprecedented and surprising property of contact with water causing an improvement to the ultraviolet-ray protective ability. It is preferable for the cosmetic to contain an (C) oily component having IOB of 0.5 or higher.

7 Claims, 1 Drawing Sheet

(56) References Cited

FOREIGN PATENT DOCUMENTS

| | | |
|---|---|---|
| JP | 2007-63145 | 3/2007 |
| JP | 2007-332037 | 12/2007 |
| JP | 2008-106060 | 5/2008 |
| JP | 2009227645 A * | 10/2009 |
| JP | 2012-140404 | 7/2012 |
| JP | 2013-170145 | 9/2013 |
| JP | 2015-30723 | 2/2015 |
| WO | WO 2012/090581 | 5/2012 |

OTHER PUBLICATIONS

EP 15855168.9, Office Action dated May 4, 2018, 7 pages—English.
Japanese Patent Appln. No. 2016-556662, Notice of Reasons for Refusal, dated Mar. 17, 2020, 6 pages—English, 6 pages—Japanese.
Chinese Patent Application Serial No. CN 201580058447.7, Office Action dated Aug. 29, 2019, 5 pages—Japanese, 3 pages—English.

* cited by examiner

OIL-IN-WATER EMULSION SUNSCREEN COSMETIC

CROSS REFERENCE TO RELATED APPLICATIONS

This application relates to, and claims priority from Ser. No.: PCT/JP2015/080765 filed Oct. 30, 2014, the entire contents of which are incorporated herein by reference, which in turn claims priority from JP Ser. No.: 2015-181984 filed Sep. 15, 2015 and from JP Ser. No.:2014-222963 filed Oct. 31, 2014.

FIGURE SELECTED FOR PUBLICATION

FIG. 1(A)-1(F)

BACKGROUND OF THE INVENTION

Field of the Invention

The present invention relates to an oil-in-water emulsion sunscreen cosmetic. More specifically, the invention relates to an oil-in-water emulsion sunscreen cosmetic having the unprecedented property wherein the UV protective effect improves relative to the effect immediately after application, by coming into contact with water, sweat or the like.

Description of the Related Art

Protecting the skin from harm due to UV rays is an important problem in skin care and body care, and various types of UV-care cosmetics have been developed for minimizing the detrimental impact that UV rays have on the skin. Sunscreen cosmetics, which are a type of UV-care cosmetic, protect the skin from harm due to UV rays by blocking UVA and UVB from reaching the skin, by blending in UV absorbing agents or UV scattering agents (Non-patent Document 1). Recently, it has come to be considered important to protect the skin from UV rays, not only under the severe UV conditions that occur during outdoor activities such as when swimming in a pool or in the sea during the summer or when skiing during the winter, but also in everyday life, and has become desirable for normal skin-care cosmetics to have a UV protective effect.

As the format for sunscreen cosmetics, many preparations are in the form of emulsions, and instability of emulsification can lead to a reduced UV protective effect. Patent Document 1 describes that, by blending in free fatty acids having 14 to 24 carbon atoms, the storage stability was improved and decreases in the UV protective effect due to long-term storage were suppressed.

However, even if the UV protective effect is maintained until immediately before use, if a sunscreen cosmetic that has been applied to the skin comes into contact with water or sweat, the UV absorbing agent or the UV scattering agent may flow out from the applied cosmetic, and decreases in the UV protective effect cannot be avoided. Therefore, various attempts have been made to prevent the outflow of UV protective agents, such as by improving the water resistance or the film strength of sunscreen cosmetics.

For example, Patent Document 2 discloses a water-in-oil emulsion composition comprising a water-swellable clay mineral, a quaternary ammonium salt-type cationic surfactant, a polyoxyalkylene-modified organopolysiloxane, a water phase, and an organic silicone resin represented by the general formula $RnSiO(4-n)/2$, and proposes to improve the water resistance and the water repellence so that the UV absorbing agent is held on the skin for a long time, by blending in the organic silicone resin.

Additionally, Patent Document 3 discloses a water-in-oil emulsion cosmetic comprising an anti-UV agent, an organically modified clay mineral, a volatile component, a spherical resin powder and a film-forming agent, and proposes to prevent the rubbing away of powders or their secondary adhesion to clothes, by blending in a film-forming agent.

Additionally, oil-in-water emulsions are also widely used as sunscreen cosmetics because they provide a fresh feeling in use. However, oil-in-water emulsion cosmetics have inferior water resistance compared to those of the water-in-oil type, and they easily undergo decreases in UV protective effect due to the outflow of UV absorbing agents or UV scattering agents. Therefore, there have been attempts to improve the water resistance by blending in a film-forming agent (Patent Document 4), and to improve the UV protective effect by blending in a high concentration of UV absorbing agents (Patent Document 5).

However, cosmetics that are applied to the skin are exposed to various forms of moisture, both from the inside and the outside of the applied film, including sweat that is secreted from the skin and moisture, such as seawater, from the external environment, so it is difficult to entirely stop the outflow of UV absorbing agents or UV scattering agents, even when blending in high concentrations of film-forming agents or resins for imparting water resistance. Additionally, it was thought that even if the outflow of UV absorbing agents could be completely prevented, the resulting UV protective effects could never exceed the effects immediately after application.

Furthermore, when blending in a high concentration of a silicone resin, a film-forming agent or the like, there can be problems in connection with properties other than the UV protective effect, such as the sense of filminess of the applied cosmetic becoming strong and detracting from the feeling in use, the cosmetic becoming difficult to spread at the time of application, and the cosmetic not being easily removable using a normal detergent or soap, and requiring the use of a special cleansing agent.

RELATED ART DOCUMENTS

Patent Documents

Patent Document 1: JP 2015-30723 A
Patent Document 2: JP H1-180237 A
Patent Document 3: JP H8-217619 A
Patent Document 4: JP 2004-91377 A
Patent Document 5: JP 2012-140404 A
Non-patent Document 1: Shin-keshohingaku, 2nd edition, edited by Takeo Mitsui, 2001, published by Nanzando, pp. 497-504.

ASPECTS AND SUMMARY OF THE INVENTION

Problems to be Solved by the Invention

The present invention is based on the discovery, during the process of carrying out research into developing a sunscreen cosmetic having a strong UV protective effect, of a phenomenon wherein contact with water, sweat or the like did not reduce the UV protective effect but rather improved the effect, and has the purpose of providing a sunscreen cosmetic having the unprecedented and innovative property wherein the UV protective effect is improved by coming into contact with moisture.

Means for Solving the Problems

As a result of carrying out diligent study into solving the aforementioned problems, the present inventors discovered that a sunscreen cosmetic having novel properties and achieving the aforementioned purpose can be obtained by blending a UV absorbing agent and/or a UV scattering agent with a fatty acid, and setting the neutralization rate of the fatty acid so as to be a prescribed value or less, thereby completing the present invention.

In other words, the present invention provides an oil-in-water emulsion sunscreen cosmetic comprising (A) a UV protective agent, and (B) a fatty acid that is solid at room temperature, wherein the neutralization rate of the fatty acid is 51% or less.

Effects of the Invention

Due to the above-mentioned features, the UV protective effect of the present invention after coming into contact with water, sweat or the like is significantly improved as compared with the effect immediately after application of the cosmetic to the skin. In other words, the oil-in-water emulsion sunscreen cosmetic according to the present invention is an innovative sunscreen cosmetic wherein the UV protective effect is improved upon coming into contact with moisture, which was considered to be a cause of deterioration in conventional sunscreen cosmetics, thus having properties that are the exact opposite of what was conventionally expected.

Furthermore, the sunscreen cosmetic of the present invention achieves excellent UV protective effects even without blending in a high concentration of silicone resins or film-forming agents in order to improve the water resistance, so there is no sense of filminess and the cosmetic can be easily spread at the time of application. Additionally, the cosmetic possesses the properties that are inherent in oil-in-water emulsion cosmetics, thus not only providing a fresh feeling at the time of use, but also having an excellent sensation of use lacking stickiness or oiliness, and being easily removable using a normal detergent or soap.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 1A-1F are microscope photographs illustrating the cross sections of a cosmetic film immediately after application of the cosmetic of Example 19 onto a simulated skin substrate (a PMMA (polymethyl methacrylate) substrate having roughness) and after immersion in water for 30 minutes.

The photographs show that the thicknesses of the films, which are not uniform at the time of application, are made uniform after immersion in water.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

MODES FOR CARRYING OUT THE INVENTION

The action mechanism by which the sunscreen cosmetic of the present invention achieves the characteristic property of improving the UV protective effect upon coming into contact with water has not been entirely explained at the current time, but the following hypotheses can be made.

First, it is thought that, immediately after the sunscreen cosmetic of the present invention having the above-mentioned features has been applied to the skin, there are non-uniformities in the film containing the UV protective agent. However, when this film comes into contact with moisture such as with tap water, seawater or sweat, minerals such as calcium ions and magnesium ions contained in the moisture can interact with the fatty acid components, thereby raising the water repellence of the film and improving the uniformity of the film compared to the state immediately after application. It is known that the uniformity of the film of a sunscreen cosmetic is important for UV protective effects, and as a result, UV protective effects that are higher than those immediately after application are achieved, while simultaneously preventing the deterioration of the UV protective effect due to the outflow of the UV protective agent.

In fact, it was confirmed, by observation by electron microscopy and the like, that the uniformity of the film (the denseness of the surface and the homogeneity of the film itself) was better after coming into contact with water, as compared with the state immediately after application of the sunscreen cosmetic of the present invention. Conversely, with conventional sunscreen cosmetics, the uniformity of the film is reduced upon coming into contact with moisture. According to observations made by the present inventors, even in the case of films formed from sunscreen cosmetics having the same composition, films that are uniform overall have a much better UV protective effect in comparison to non-uniform films. This is believed to be due to the fact that the UV protective effect does not improve additively with increasing film thickness, but rather improves synergistically in proportion to the film thickness.

Next, the components contained in the sunscreen cosmetic of the present invention will be described in detail.

<(A) UV Protective Agent>

The (A) UV protective agent (hereinafter sometimes referred to simply as "component (A)") that is blended in the oil-in-water emulsion sunscreen cosmetic according to the present invention refers to a UV absorbing agent and/or a UV scattering agent that is normally used by being blended into a sunscreen cosmetic.

The UV absorbing agent used in the present invention is not particularly limited, but specific examples include organic UV absorbing agents such as ethylhexyl methoxycinnamate, octocrylene, dimethicodiethyl benzal malonate, polysilicone-15, t-butyl methoxydibenzoyhnethane, ethylhexyl triazone, diethylamino hydroxybenzoyl hexyl benzoate, bis-ethylhexyloxyphenol methoxyphenyl triazine, oxybenzone-3, methylene bis-benzotriazolyl tetramethylbutylphenol, phenylbenzimidazole sulfonic acid, homosalate and ethylhexyl salicylate.

The UV scattering agent used in the present invention is not particularly limited, but specific examples include fine particulate metal oxides such as, for example, zinc oxide, titanium oxide, iron oxide, cerium oxide and tungsten oxide.

The UV scattering agent may be non-surface-treated or surface-treated using various methods, and the surface-treating agents may be those that are commonly used in the field of cosmetics, for example, alkoxysilanes such as octyltriethoxysilane, fatty acid esters of dextrin such as dextrin palmitate, and fatty acids such as stearic acid.

The blended amount of the component (A) is preferably at least 5% by mass, more preferably 5% to 40% by mass, and even more preferably 6% to 20% by mass with respect to the total amount of the oil-in-water emulsion sunscreen cosmetic. If the blended amount of the component (A) is less than 5% by mass, then it is difficult to obtain adequate UV protective effects, and even if blended in excess of 40% by mass, an increase in the UV protective effects commensurate with the blended amount cannot be expected, and a tendency for the stability and the sensation of use to worsen is observed.

The UV protective agent (component (A)) in the present invention includes embodiments containing only a UV absorbing agent, embodiments containing only a UV scattering agent, and embodiments containing both a UV absorbing agent and the UV scattering agent.

<(B) Fatty Acid>

The (B) fatty acid (hereinafter sometimes referred to simply as "component (B)") used in the present invention is not particularly limited as long as it is of a type that can be used in cosmetics or the like, and may be selected from among linear or branched fatty acids having saturated or unsaturated hydrocarbon groups.

Particular examples include linear higher fatty acids that are solid at room temperature and that have 8 to 22 carbon atoms such as, for example, lauric acid, myristic acid, palmitic acid, stearic acid, behenic acid and oleic acid. Of these, one or more fatty acids selected from the group consisting of stearic acid, palmitic acid and behenic acid are particularly preferable.

Additionally, the fatty acids used in the present invention are partially neutralized (with a neutralization rate of 51% or less) by counterions (cations).

The "neutralization rate (of the fatty acid)" in the present specification is defined as the numerical value represented by the following formula (A):

$$[(Eb-Ea'')/(Ea')]\times 100(\%) \quad\quad (A)$$

where Ea' represents the total equivalent number of fatty acids blended into the oil-in-water emulsion cosmetic, Ea" represents the total equivalent number of substances after removing the fatty acids from the acidic substances in the cosmetic, and Eb represents the total equivalent number of basic substances blended into the cosmetic.

In the cosmetic of the present invention, the basic substance that is used as the neutralizing agent of the fatty acid (component (B)) is a substance capable of supplying counterions (cations) that can neutralize the fatty acid anions, and may be an inorganic base, an organic base, a cationic polymer or the like that can be blended into a cosmetic product or the like, and is not particularly limited.

Typical examples of inorganic bases include sodium hydroxide, potassium hydroxide and ammonium chloride.

Examples of organic bases include amines such as, for example, monoethanolamine, diethanolamine, triethanolamine, aminomethyl propanediol, 2-amino-2-methylpropanol (AMP), triisopropanolamine (TIPA), tris[(2-hydroxy)-1-propyl]amine, 2-amino-2-methyl-1,3-propanediol (AMPD), 2-amino-2-hydroxymethyl-1,3-propanediol and N-methylglucamine, and basic amino acids such as, for example, arginine and lysine.

The cationic polymer is not particularly limited as long as it is a cationic polymer that can be used in a cosmetic or in an external agent for the skin. Specific examples include cationized cellulose derivatives [for example, quaternary nitrogen-containing cellulose ethers ("Polymer JR-400", "Polymer JR-125" or "Polymer JR-300M" (all manufactured by Union Carbide of the US), cationized guar gum, cationized locust bean gum, cationized tara gum, homopolymers of diallyl quaternary ammonium salts, diallyl quaternary ammonium salt/acrylamide copolymers [e.g., dimethyldiallylammonium chloride/acrylamide copolymers ("Merquat 2200" manufactured by Nalco), quaternized polyvinylpyrrolidone derivatives, polyglycol-polyamine condensates, vinylimidazolium trichloride/vinylpyrrolidone copolymers, hydroxyethylcellulose/dimethyldiallyl ammonium chloride copolymers, vinylpyrrolidone/quaternized dimethylaminoethyl methacrylate copolymers, polyvinylpyrrolidone/alkylaminoacrylate copolymers, polyvinylpyrrolidone/alkylaminoacrylate/vinylcaprolactam copolymers, vinylpyrrolidone/methacrylamidopropyl trimethylammonium chloride copolymers, alkylacrylamide/acrylate/alkylaminoalkylacrylamide/polyethylene glycol methacrylate copolymers, adipic acid/dimethylamino hydroxypropyl ethylene triamine copolymers, and vinylpyrrolidone/N,N-dimethylaminoethyl methacrylate/stearyl acrylate/tripropylene glycol diacrylate copolymers ("CU Polymer (D)", manufactured by Osaka Organic Chemical Industry). However, the invention is not limited to these examples.

In the present invention, by setting the neutralization rate of the fatty acid to 51% or less, it is possible to obtain the unprecedented property wherein the UV protective effect is improved by coming into contact with water. A "fatty acid having a neutralization rate of 51% or less" includes non-neutralized fatty acids and fatty acids neutralized to a neutralization rate of 51% or less as calculated in accordance with the above-mentioned formula (A). As a numerical range, the neutralization rate of the fatty acids in the present invention is 0% to 51%, and all numerical values included in this range, for example, any value such as 0.001%, 0.01%, 0.1%, 0.5%, 1%, 5%, 10%, 15%, 20%, 25%, 30%, 35%, 40%, 45% or 50%, and all numerical ranges having these values as lower limit values or upper limit values may be included.

The blended amount of the component (B) in the cosmetic of the present invention need only satisfy the below-mentioned blending ratio requirement with respect to the blended amount of the UV protective agent that is blended together therewith, and the amount blended is normally in the range of 1% by mass to 40% by mass. Preferably, the blended amount is more than 5% by mass, and 40% by mass or less. It goes without saying that the blended amount may take any value within the aforementioned range. In this case, "more than 5% by mass" refers to an amount that does not include 5% by mass as the lower limit value of the blended amount, but that may include a greater blended amount, such as 5.1% by mass or more, 5.5% by mass or more, 6% by mass or more, 7% by mass or more, 8% by mass or more, 9% by mass or more or 10% by mass or more. On the other hand, the upper limit value of the blended amount may be set to 40% by mass or less, 35% by mass or less, 30% by mass or less, 28% by mass or less, 25% by mass or less, 22% by mass or less, or 20% by mass or less.

On the other hand, the amount of the basic substance (neutralizing agent) that is blended in order to neutralize the fatty acid may be calculated on the basis of the above-mentioned formula (A) so that the fatty acid neutralization rate is 51% or less, based on the blended amount of the fatty acid and the blended amount of other acidic substances that are included.

In order to reliably achieve the desired effects in the cosmetic of the present invention, it is necessary to set the blending ratio ((A)/(B)) between the UV absorbing agent and/or the UV scattering agent (component (A)) and component (B) so as to be at least 0.1 and less than 10.0. If this ratio becomes 10.0 or more, there may be cases in which the effect specific to the present invention, that of improving the UV protective effect when coming into contact with moisture, cannot be obtained. It goes without saying that "less than 10.0" does not include 10.0, but does include all smaller values. This blending ratio may be any numerical value or any numerical range (e.g., 0.1 to 9.0, 0.2 to 8.0 or 0.3 to 7.0) that is at least 0.1 and less than 10.0. That is, the upper limit of the blending ratio can be set to 9.9, 9.8, 9.7, 9.6, 9.5, 9.0, 8.0, 7.0 or 6.0, and the lower limit can be set to 0.1, 0.15, 0.2, 0.3 or 0.4.

<(C) Oil Having an IOB of 0.5 or More>

The oil-in-water emulsion sunscreen cosmetic of the present invention, by further blending (C) an oil having an IOB of at least 0.5 in addition to the above-mentioned essential components, is able to raise the UV protective effect before coming into contact with moisture (hereinafter referred to as the initial UV protective effect), and to further raise the margin of improvement and the speed of improvement of the UV protective effect before and after bathing in water.

The IOB value refers to the ratio (inorganic/organic balance) of an inorganic value (IV) to an organic value (OV) in an organic conceptual diagram, i.e. "inorganic value (IV)/organic value (OV)". An organic conceptual diagram is a diagram wherein the source of all organic compounds is assumed to be methane (CH4), all other compounds are considered to be derivatives of methane, standard numerical values are assigned to the number of carbon atoms, substituent groups, transformations and rings, and their score is added up to determine the organic value and the inorganic value, which are then plotted on the diagram with the organic value on the X axis and the inorganic value on the Y axis (see Yuki-gainen-zu—kiso to oyo—(Yoshio Koda, Sankyo Shuppan, 1984)).

The (C) oil having an IOB of at least 0.5 (hereinafter sometimes referred to as "component (C)") used in the present invention may be of any type that has conventionally been used in cosmetics, including ester oils such as diethoxyethyl succinate and alkylene polyglycol dineopentanoate, and alkylene oxide derivatives including polyalkylene glycols such as polyethylene glycol (PEG), polypropylene glycol (PPG) and polybutylene glycol (PBG).

In the present invention, it is preferable to use an alkylene oxide derivative, preferably a random alkylene oxide derivative represented by the following formula (I).

$$R^1O\text{-}[(AO)_m(EO)_n]\text{-}R^2 \qquad (I)$$

In the formula, AO represents an oxyalkylene group having 3 to 4 carbon atoms, EO represents an oxyethylene group, and m and n respectively represent the average added number of moles of oxyalkylene groups and oxyethylene groups, such that $1 \leq m \leq 70$ and $1 \leq n \leq 70$. The ratio of oxyethylene groups with respect to the total amount of oxyalkylene groups having 3 to 4 carbon atoms and oxyethylene groups is 20% to 80% by mass. The oxyalkylene groups having 3 to 4 carbon atoms and the oxyethylene groups may be added in blocks or added randomly. R1 and R2 may be identical or different, and are hydrogen atoms or hydrocarbon groups having 1 to 4 carbon atoms, such that the ratio of the number of hydrogen atoms with respect to the number of hydrocarbon groups in R1 and R2 is 0.15 or less.

In the alkylene oxide derivative of formula (I), AO is an oxyalkylene group having 3 to 4 carbon atoms, specific examples of which include oxypropylene groups, oxybutylene groups, oxyisobutylene groups, oxytrimethylene groups and oxytetramethylene groups. Oxypropylene groups and oxybutylene groups are preferable. EO is an oxyethylene group. m is the average added number of moles of the oxyalkylene groups having 3 to 4 carbon atoms, where $1 \leq m \leq 70$, and preferably $2 \leq m \leq 50$. n is the average added number of moles of the oxyethylene groups, where $1 \leq n \leq 70$, and preferably $5 \leq n \leq 55$.

Additionally, the ratio of the oxyethylene groups with respect to the total of oxyalkylene groups having 3 to 4 carbon atoms and oxyethylene groups is preferably 20% to 80% by mass. The order of addition of the ethylene oxides and the alkylene oxides having 3 to 4 carbon atoms is not particularly specified. Additionally, the oxyethylene groups and the oxyalkylene groups having 3 to 4 carbon atoms may be added in the form of blocks or added randomly. Those that are added randomly are preferred.

R1 and R2 are hydrogen atoms or hydrocarbon groups having 1 to 4 carbon atoms, among which examples of hydrocarbon groups include alkyl groups such as methyl groups, ethyl groups, n-propyl groups, isopropyl groups, n-butyl groups, sec-butyl groups and tert-butyl groups. Methyl groups and ethyl groups are preferred. There is a tendency for the effects of the present invention to be reduced when the hydrocarbon groups have 5 or more carbon atoms. R1 and R2 may be identical or different.

There may be just one type each of R1 and R2, there may be a mixture of hydrogen atoms and hydrocarbon groups having 1 to 4 carbon atoms, or there may be a mixture of different hydrocarbon groups having 1 to 4 carbon atoms. However, of the hydrocarbon groups in R1 and R2, the ratio of the presence of hydrocarbon groups and hydrogen atoms, i.e. the ratio Y/X of the number of hydrogen atoms (Y) to the number of hydrocarbon groups (X), should be 0.15 or less, preferably 0.06 or less.

The alkylene oxide derivative of formula (I) can be manufactured by a publicly known method. For example, it may be obtained by addition polymerization of alkylene oxides having 3 to 4 carbon atoms and ethylene oxides to compounds having hydroxyl groups, followed by an ether reaction by a halogenated alkyl in the presence of an alkali catalyst.

Specific examples of the alkylene oxide derivative of formula (I) include POE (9) POP (2) dimethyl ether, POE (14) POP (7) dimethyl ether, POE (10) POP (10) dimethyl ether, POE (6) POP (14) dimethyl ether, POE (15) POP (5) dimethyl ether, POE (25) POP (25) dimethyl ether, POE (7) POP (12) dimethyl ether, POE (22) POP (40) dimethyl ether, POE (35) POP (40) dimethyl ether, POE (50) POP (40) dimethyl ether, POE (55) POP (30) dimethyl ether, POE (30) POP (34) dimethyl ether, POE (25) POP (30) dimethyl ether, POE (27) POP (14) dimethyl ether, POE (55) POP (28) dimethyl ether, POE (36) POP (41) dimethyl ether, POE (7) POP (12) dimethyl ether, POE (17) POP (4) dimethyl ether, POE (9) POB (2) dimethyl ether, POE (14) POB (7) dimethyl ether, POE (10) POP (10) diethyl ether, POE (10) POP (10) dipropyl ether and POE (10) POP (10) dibutyl ether. In the present invention, a polyoxyethylene (POE)/polyoxypropylene (POP) dimethyl ether is preferably used, but the invention is not limited thereto.

The above-mentioned POE, POP and POB are respectively abbreviations for polyoxyethylene, polyoxypropylene and polyoxybutylene.

The alkylene oxide derivative in the present invention includes polyalkylene glycols such as polyethylene glycol (PEG), polypropylene glycol (PPG) and polybutylene glycol (PBG).

The polyalkylene glycol in the present invention includes polyoxybutylene polyoxypropylene glycols such as polyoxybutylene (9) polyoxypropylene (1) glycol, and polyoxyethylene polyoxypropylene glycols, and is appropriately selected from the group consisting of those that can be used in external agents for the skin such as cosmetics. Those having a molecular weight of at least 300 are preferable, and those having a molecular weight of at least 1000 are more preferable. Although the upper limit value for the molecular weight is not particularly limited, those having a molecular weight, for example, of 20,000 or less, 5,000 or less or 2,500 or less are preferably used.

The alkylene oxide derivatives in the present invention may be of one or more arbitrarily selected types, but polyoxyethylene/polyoxypropylene dimethyl ethers which are alkylene oxide derivatives of formula (I), particularly polyoxyethylene (14) polyoxypropylene (7) dimethyl ether, are included.

The upper limit for the IOB value of component (C) in the cosmetic of the present invention is not particularly limited, but for example, an oil having an IOB of approximately 3.0 or less is preferably used.

The blended amount when including the component (C) is not particularly limited, but by blending in an amount that is in the range, for example, of 0.005% to 20% by mass, 0.5% to 10% by mass or 0.1% to 5% by mass, the time between coming into contact with moisture and achieving the UV protective effect improvement effect can be shortened.

The oil-in-water emulsion sunscreen cosmetic of the present invention may, in addition to the above-mentioned essential components, have components that are normally used in cosmetics, for example, humectants, thickeners, powders, alcohols, natural polymers, synthetic polymers, sugars, antioxidants, buffering agents, various extracts, stabilizers, preservatives, pigments and fragrances, appropriately blended within a range not compromising the effects of the present invention.

However, if more than 5.0% by mass of a surfactant is blended, then the formed film itself may be washed away upon coming into contact with water, so it is preferable for the blended amount of the surfactant to be 5.0% by mass or less, and the present invention includes embodiments not containing surfactants.

The method for manufacturing the oil-in-water emulsion sunscreen cosmetic of the present invention is not particularly limited, and it may, for example, be prepared by separately mixing the components constituting the oil phase and the components constituting the water phase, then adding the oil phase to the water phase, and stirring to emulsify.

The composition of the present invention has the fresh feeling in use and excellent washability that are inherent in oil-in-water emulsions, and achieves the characteristic property wherein the UV protective effect improves upon coming into contact with water, so the composition is particularly suitable for use as a novel type of oil-in-water emulsion sunscreen cosmetic.

The oil-in-water emulsion sunscreen cosmetic of the present invention may be offered not only in the form, for example, of a sunscreen cream, a sunscreen emulsion or a sunscreen lotion, but also may be used as a foundation, a makeup base, a makeup cosmetic, a hair cosmetic or the like having a sunscreen effect.

EXAMPLES

The present invention will be further explained by describing examples below, but the present invention is not to be construed as being limited thereto. Where not particularly noted otherwise, blended amounts are indicated as a percentage by mass with respect to the total mass.

EXAMPLES AND COMPARATIVE EXAMPLES

The oil-in-water emulsion sunscreen cosmetics indicated in the examples and the comparative examples were prepared by adding an oil phase obtained by appropriately heating and dissolving the oil-based components to a water phase separately obtained by warming and dissolving the water-based components as needed, then emulsifying by a stirring process.

Measurement of UV Protective Effect

The cosmetics (samples) of the examples were dripped in an amount of 2 mg/cm2 onto measurement plates (S plates) (5×5 cm V-groove PMMA plates, SPFMASTER-PA01), applied using a finger for 60 seconds, and dried for 15 minutes, after which the absorbances thereof were measured using a Hitachi U-3500 self-recording spectrophotometer. Using glycerin which does not absorb UV rays as a control, the absorbance (Abs) was calculated from the following formula:

Abs=−log(T/To)

where T represents the transmittance of the sample and To represents the transmittance of the glycerin.

The measured plates were well-immersed in water having a hardness of 50 to 500, then stirred in the water for 30 minutes (300 rpm using a 3-1 motor). Thereafter, the samples were dried for about 15 to 30 minutes until the water droplets on the surfaces disappeared, and the absorbances were measured again, and the integral values of the absorbance (Abs) before and after immersion in water were used to calculate the Abs change rate (the below formula) as the UV protective effect improvement effect.

UV Protective Effect Improvement Effect:

Abs change rate (%)=(integral of Abs after water immersion)/(integral of Abs before water immersion)×100

In the present invention, the UV protective effect is defined as having improved when the Abs change rate exceeds 100(%).

Examples 1 and 2, and Comparative Examples 1-5

Cosmetics having the compositions shown in the following Table 1 were prepared, and their Abs integral values before and after water immersion, and their change rates, were determined.

TABLE 1

| Component | Ex. 1 | Ex. 2 | Comp. Ex. 1 | Comp. Ex. 2 | Comp. Ex. 3 | Comp. Ex. 4 | Comp. Ex. 5 |
|---|---|---|---|---|---|---|---|
| Purified water | bal | bal | bal | bal | bal | bal | bal |
| 2-Ethylhexyl para-methoxycinnamate | 7.5 | 7.5 | 7.5 | 7.5 | 7.5 | 7.5 | 7.5 |
| Stearic acid | 10 | 10 | 10 | 10 | 10 | 10 | 10 |
| Potassium hydroxide | 0.5 | 1 | 1.2 | 1.4 | 2 | 3 | 4 |
| Total | 100 | 100 | 100 | 100 | 100 | 100 | 100 |
| Fatty acid neutralization rate (%) | 25.4 | 50.7 | 60.8 | 71.0 | 101.4 | 152.1 | 202.8 |
| Abs integral before water immersion | 63.1 | 80.9 | 56.8 | 41.9 | 64.8 | 56.5 | 58.4 |
| Abs integral after water immersion | 78.1 | 100.1 | 56.0 | 24.7 | 20.1 | 29.8 | 25.9 |
| Abs change rate (%) before/after water immersion | 123.8 | 123.7 | 98.6 | 59.0 | 31.0 | 52.7 | 44.3 |

As shown in Table 1, even if the blended amounts of the (A) UV protective agent and the (B) fatty acid are the same, if the neutralization rate of the (B) fatty acid exceeds 51% (Comparative Examples 1-5), the UV protective effect becomes lower after water immersion. In contrast, when the neutralization rate of the (B) fatty acid is 51% or less (Examples 1 and 2), the UV protective effect after water immersion is increased by approximately 24% compared with that before water immersion.

Examples 3 and 4

Cosmetics having the compositions shown in the following Table 2 were prepared, and their Abs integral values before and after water immersion, and their change rates, were determined.

TABLE 2

| Component | Ex. 1 | Ex. 3 | Ex. 4 |
|---|---|---|---|
| Purified water | bal | bal | bal |
| 2-Ethylhexyl para-methoxycinnamate | 7.5 | 7.5 | 7.5 |
| Stearic acid | 10 | 10 | 10 |
| Polyoxybutylene (9) polyoxypropylene (1) glycol | — | 3 | — |
| Polyoxyethylene (14) polyoxypropylene (7) dimethyl ether | — | — | 0.1 |
| Potassium hydroxide | 0.5 | 0.5 | 0.5 |
| Total | 100 | 100 | 100 |
| Fatty acid neutralization rate (%) | 25.4 | 25.4 | 25.4 |
| Abs integral before water immersion | 63.1 | 76.7 | 81.1 |
| Abs integral after water immersion | 78.1 | 103.9 | 105.5 |
| Abs change rate (%) before/after water immersion | 123.8 | 135.5 | 130.0 |

As shown in Table 2, compared with the case wherein only component (A) and component (B) are included (Example 1), when (C) an oil having an IOB of at least 0.5 was further included (Examples 3 and 4), the UV protective effect before water immersion significantly improved, and the margin of improvement of the UV protective effect before and after water immersion (Abs change rate) also significantly increased.

Examples 5 to 15 and Comparative Example 6

Cosmetics having the compositions shown in the following Tables 3 and 4 were prepared, and their Abs integral values before and after water immersion, and their change rates, were determined.

TABLE 3

| Component | Ex. 5 | Ex. 6 | Ex. 7 | Ex. 8 | Ex. 9 | Comp. Ex. 6 |
|---|---|---|---|---|---|---|
| Ion-exchanged water | bal | bal | bal | bal | bal | bal |
| Potassium hydroxide | 0.5 | 0.5 | 0.25 | 0.15 | 0.1 | 0.05 |
| Behenic acid | 5 | — | — | — | — | — |
| Stearic acid | 15 | 15 | 5 | 3 | 2 | 1 |
| Cetanol | 0.5 | 0.5 | 0.5 | 0.5 | 0.5 | 0.5 |
| Methylparaben | 0.3 | 0.3 | 0.3 | 0.3 | 0.3 | 0.3 |
| Polyoxyethylene (14) polyoxypropylene (7) dimethyl ether | 0.1 | 0.1 | 0.1 | 0.1 | 0.1 | 0.1 |
| 2-Ethylhexyl para-methoxycinnamate | 7.5 | 7.5 | 7.5 | 7 | 8 | 8 |
| Diethylamino hydroxybenzoyl hexyl benzoate | 2 | 2 | 2 | 2 | 2 | 2 |
| Total | 100 | 100 | 100 | 100 | 100 | 100 |
| Fatty acid neutralization rate (%) | 13.3 | 16.9 | 25.4 | 25.4 | 25.4 | 25.4 |
| [UV-protecting agent]/[fatty acid] blending ratio | 0.475 | 0.633 | 1.9 | 3.3 | 5 | 10 |
| Abs integral before water immersion | 91.7 | 106.2 | 86.4 | 111.7 | 107.4 | 105.8 |
| Abs integral after water immersion | 116.5 | 139.7 | 100.0 | 158.4 | 148.3 | 102.0 |
| Abs change rate (%) before/after water immersion | 127.0 | 131.5 | 115.7 | 141.8 | 138.0 | 96.4 |

TABLE 4

| Component | Ex. 10 | Ex. 11 | Ex. 12 | Ex. 13 | Ex. 14 | Ex. 15 |
|---|---|---|---|---|---|---|
| Ion-exchanged water | bal | bal | bal | bal | bal | bal |
| 1,3-Butylene glycol | 8 | 8 | 8 | 8 | 8 | 8 |
| Ethanol | 8 | 8 | 8 | 8 | 8 | 8 |
| Hydroxyethylcellulose | — | — | — | — | — | 0.3 |
| Carbomer | — | — | — | — | 0.1* | — |
| Potassium hydroxide | 0.5 | 0.5 | 0.5 | 0.25 | 0.3 | 0.25 |
| Palmitic acid | — | 4 | — | — | — | — |
| Stearic acid | 15 | 15 | 10 | 5 | 5 | 5 |
| Cetanol | 0.5 | 0.5 | 0.5 | 0.5 | 0.5 | 0.5 |
| Methylparaben | 0.3 | 0.3 | 0.3 | 0.3 | 0.3 | 0.3 |
| Phenoxyethanol | 0.2 | 0.2 | 0.2 | 0.2 | 0.2 | 0.2 |
| Polyoxyethylene (14) polyoxypropylene (7) dimethyl ether | 0.5 | 0.5 | 0.5 | 0.5 | 0.5 | 0.5 |
| Polyoxybutylene (9) polyoxypropylene (1) glycol | 0.5 | 0.5 | 0.5 | 0.5 | 0.5 | 0.5 |
| 2-Ethylhexyl para-methoxycinnamate | 7.5 | 7.5 | 7.5 | 7.5 | 7.5 | 7.5 |
| Octocrylene | 5 | 5 | 5 | 5 | 5 | 5 |
| Diethylamino hydroxybenzoyl hexyl benzoate | 2 | 2 | 2 | 2 | 2 | 2 |
| Total | 100 | 100 | 100 | 100 | 100 | 100 |
| Fatty acid neutralization rate (%) | 16.9 | 13.0 | 25.4 | 25.4 | 25.4 | 25.4 |
| Abs integral before water immersion | 85.2 | 80.2 | 108.7 | 113.0 | 125.5 | 115.1 |
| Abs integral after water immersion | 127.3 | 126.1 | 138.0 | 180.4 | 157.2 | 145.6 |
| Abs change rate (%) before/after water immersion | 149.4 | 157.2 | 127.0 | 159.6 | 125.3 | 126.5 |

*Calculated as the amount necessary to neutralize the thickener when the ratio carbomer: sodium hydroxide = 1:0.5

As shown in Table 3 and Table 4, even if the type or the blended amount of the fatty acid or the combination with other blended components is changed, as long as the conditions recited in claim 1 are fulfilled, all of the cosmetics achieved the characteristic effect of the present invention wherein the UV protective effect is improved after water immersion as compared to before water immersion. However, in Comparative Example 6 wherein the blending ratio between the "UV protective agent" and the "fatty acid" is 10.0, the characteristic effect of the present invention, wherein the UV protective effect is improved after water immersion, was not obtained.

Examples 16 to 23

Cosmetics having the compositions shown in the following Table 5 were prepared, and their absorbance change rates before and after water immersion were determined for water immersion times of 30 seconds, 1 minute and 5 minutes. The results are shown in Table 5.

TABLE 5

| Component | Ex. 16 | Ex. 17 | Ex. 18 | Ex. 19 | Ex. 20 | Ex. 21 | Ex. 22 | Ex. 23 |
|---|---|---|---|---|---|---|---|---|
| Purified water | bal | bal | bal | bal | bal | bal | bal | bal |
| 2-Ethylhexyl para-methoxycinnamate | 7.5 | 7.5 | 7.5 | 7.5 | 7.5 | 7.5 | 7.5 | 7.5 |
| Stearic acid | 10 | 10 | 10 | 10 | 10 | 10 | 10 | 10 |
| Polyoxyethylene (14) polyoxypropylene (7) dimethyl ether | 0 | 0.1 | 1 | 5 | — | — | — | — |
| Polyoxybutylene (9) polyoxypropylene (1) glycol | — | — | — | — | 5 | — | — | — |
| Polypropylene glycol | — | — | — | — | — | 5 | — | — |
| Polyethylene glycol (molecular weight 400) | — | — | — | — | — | — | 5 | — |
| Polyethylene glycol (molecular weight 20000) | — | — | — | — | — | — | — | 5 |
| Potassium hydroxide | 0.5 | 0.5 | 0.5 | 0.5 | 0.5 | 0.5 | 0.5 | 0.5 |
| Total | 100 | 100 | 100 | 100 | 100 | 100 | 100 | 100 |
| Fatty acid neutralization rate (%) | 25.4 | 25.4 | 25.4 | 25.4 | 25.4 | 25.4 | 25.4 | 25.4 |
| Abs change rate (%) before/after water immersion: after 30 sec | 99.6 | 99.8 | 102.1 | 101.7 | 102.6 | 100.5 | 103.1 | 107.4 |
| Abs change rate (%) before/after water immersion: after 1 min | 99.8 | 108.3 | 106.4 | 109.6 | 106.5 | 103.5 | 111.0 | 114.5 |
| Abs change rate (%) before/after water immersion: after 5 min | 106.3 | 114.9 | 107.2 | 114.5 | 105.3 | 107.2 | 122.0 | 123.5 |

As is clear from the results shown in Table 5, in Example 16 which does not include an oil having an IOB of at least 0.5, the change rate exceeded 100% after 5 minutes of water immersion, whereas in Example 17 which includes 0.1% by mass of an oil having an IOB of at least 0.5, the change rate exceeded 100% after 1 minute of water immersion. Furthermore, in Examples 18 to 23 wherein the blended amounts of the oil having an IOB of at least 0.5 were 1% by mass and 5% by mass, the change rate exceeded 100% after just 30 seconds. In other words, it was confirmed that the rate of occurrence of the UV protective effect improvement effect due to water immersion was raised by adding an oil having an IOB of at least 0.5.

Examples 24 and 25

Cosmetics having the compositions shown in the following Table 6 were prepared, and their absorbance change rates before and after water immersion were determined for a water immersion time of 30 minutes. The results are shown in Table 6.

TABLE 6

| Component | Ex. 24 | Ex. 25 |
|---|---|---|
| Purified water | bal | bal |
| Ethanol | 8 | 8 |
| Glycerin | 1 | — |
| Butylene glycol | 1 | — |
| 2-Ethylhexyl para-methoxycinnamate | 7 | 7 |
| Diethylamino hydroxybenzoyl hexyl benzoate | 2 | 2 |
| 2,4-bis-[[4-(2-ethylhexyloxy)-2-hydroxy]-phenyl]-6-(4-methoxyphenyl)-1,3,5-triazine | 2 | — |
| Octocrylene | 3 | — |
| Polyoxybutylene (9) polyoxypropylene (1) glycol | 2 | 2 |
| Polyoxyethylene (14) polyoxypropylene (7) dimethyl ether | 1 | 0.5 |
| Stearic acid | 15 | 15 |
| Behenic acid | — | 5 |
| Cetanol | 0.5 | — |
| Isododecane | — | 5 |
| Titanium oxide | — | 5 |
| Potassium hydroxide | 0.5 | 0.5 |
| Methylparaben | 0.3 | 0.3 |
| Phenoxyethanol | 0.2 | 0.2 |
| Total | 100 | 100 |
| Fatty acid neutralization rate (%) | 16.9 | 13.2 |
| Abs change rate before/after water immersion | 155.3 | 141.6 |

As shown in Table 6, even if the type or the blended amount of the UV protective agent (component (A)) is changed, as long as the conditions of the present invention are fulfilled, all of the cosmetics achieved the characteristic effect of the present invention wherein the UV protective effect is improved after water immersion as compared to before water immersion.

Figure 1A:
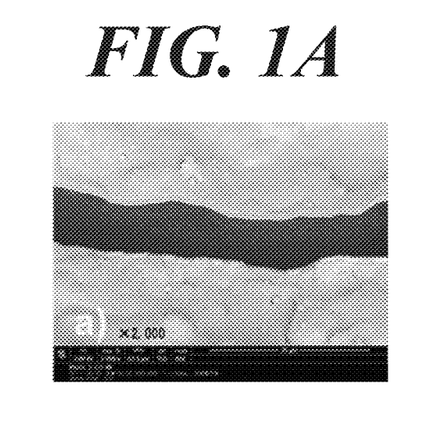
FIG. 1A is a microscope photograph illustrating the cross section of the film immediately after application to a skin ridge portion.
Figure 1B:
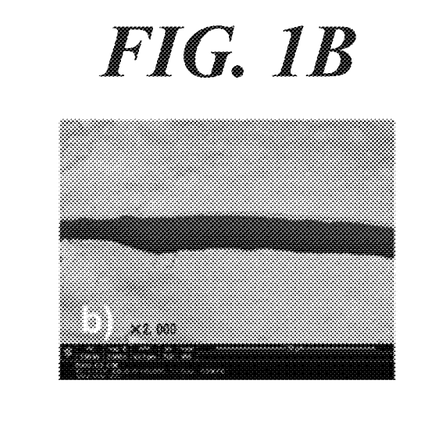
FIG. 1B is a microscope photograph illustrating the cross section of the film immediately after application to a skin ridge portion.
Figure 1C:
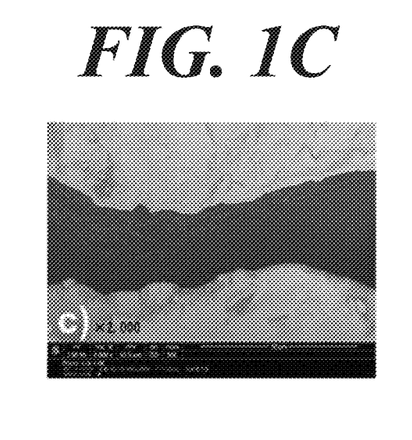
FIG. 1C is a microscope photograph illustrating the cross section of the film immediately after application to a skin groove portion.
Figure 1D:
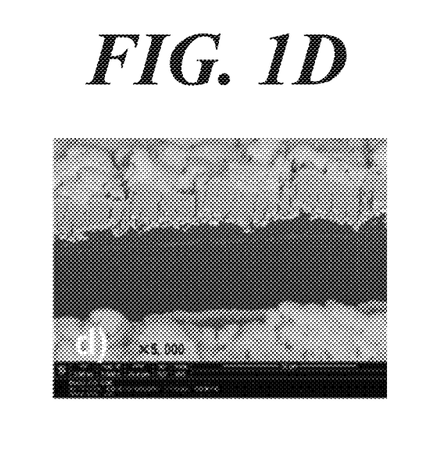
FIG. 1D is a microscope photograph illustrating the cross section of the film after application to a skin ridge portion and immersion in water.
Figure 1E:
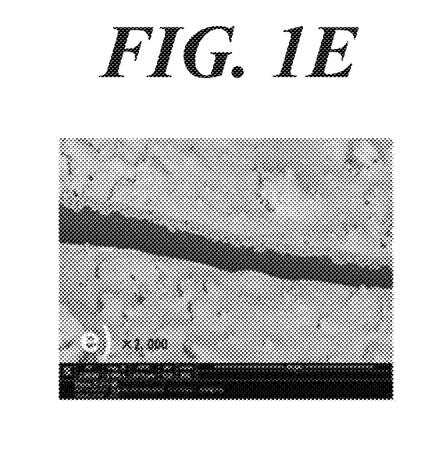
FIG. 1E is a microscope photograph illustrating the cross section of the film after application to a skin ridge portion and immersion in water.
Figure 1F:
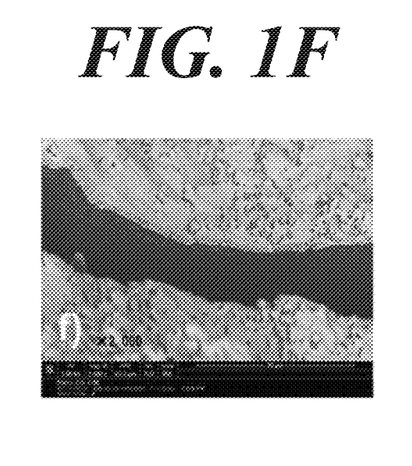
FIG. 1F is a microscope photograph illustrating the cross section of the film after application to a skin groove portion and immersion in water.

FIG. 1 shows a microscope photograph showing the cross section of a cosmetic film immediately after application of the cosmetic of Example 19 onto a simulated skin substrate (a PMMA substrate having roughness) and after immersion in water for 30 minutes. The film cross-sections immediately after application to the skin ridges (FIG. 1A, FIG. 1B) and immediately after application to the skin grooves (FIG. 1C) had considerable film roughness and the film thicknesses were not uniform, but after 30 minutes of immersion in water (skin ridges: (FIG. 1D) and (FIG. 1E); skin grooves: (FIG. 1F), it was observed that the films were made dense and uniform.

Other formulation examples (Examples 26 to 28) of the cosmetic of the present invention are shown below. The characteristic effects of the present invention wherein the UV protective effect after immersion in water was improved compared to that before immersion in water were observed in the cosmetics described in the following formulation examples.

Example 26: Sunscreen Cream

TABLE 7

| Component | Blended amount |
|---|---|
| Purified water | bal |
| Xylitol | 3 |
| Dipropylene glycol | 5 |
| 2-Ethylhexyl para-methoxycinnamate | 5 |
| Diethylamino hydroxybenzoyl hexyl benzoate | 3 |
| 2,4-bis-[[4-(2-ethylhexyloxy)-2-hydroxy]-phenyl]-6-(4-methoxyphenyl)-1,3,5-triazine | 2 |
| Octocrylene | 5 |
| Polyoxybutylene (9) polyoxypropylene (1) glycol | 2 |
| Polyoxyethylene (14) polyoxypropylene (7) dimethyl ether | 3 |
| Stearic acid | 8 |
| Behenic acid | 2 |
| Cetanol | 2 |
| Dimethicone | 5 |
| Zinc oxide | 13 |
| Titanium oxide | 5 |
| Potassium hydroxide | 0.3 |
| Phenoxyethanol | 0.5 |
| Total | 100 |

Example 27: Sunscreen Emulsion

TABLE 8

| Component | Blended amount |
|---|---|
| Purified water | bal |
| Glycerin | 7 |
| Dipropylene glycol | 5 |
| 2-Ethylhexyl para-methoxycinnamate | 7.5 |
| Diethylamino hydroxybenzoyl hexyl benzoate | 2 |
| 2,4-bis-[[4-(2-ethylhexyloxy)-2-hydroxy]-phenyl]-6-(4-methoxyphenyl)-1,3,5-triazine | 3 |
| Octocrylene | 2 |
| Polyoxybutylene (9) polyoxypropylene (1) glycol | 2 |
| Polyoxyethylene (14) polyoxypropylene (7) dimethyl ether | 3 |
| Stearic acid | 2 |
| Behenic acid | 2 |
| Myristic acid | 2 |
| Dimethicone | 5 |
| Zinc oxide | 10 |
| Sodium hydroxide | 0.3 |
| Phenoxyethanol | 0.5 |
| Hydroxyethylcellulose | 0.3 |
| Total | 100 |

Example 28: Sunscreen Emulsion

TABLE 9

| Component | Blended amount |
|---|---|
| Purified water | bal |
| Glycerin | 7 |
| Dipropylene glycol | 5 |
| 2-Ethylhexyl para-methoxycinnamate | 7.5 |
| Diethylamino hydroxybenzoyl hexyl benzoate | 2 |
| 2,4-bis-[[4-(2-ethylhexyloxy)-2-hydroxy]-phenyl]-6-(4-methoxyphenyl)-1,3,5-triazine | 3 |
| 2,4,6-tris[4-(2-ethylhexyloxycarbonyl)anilino]1,3,5-triazine | 3 |
| Polysilicone-15 | 2 |
| Polyoxypropylene glycol (*) | 2 |
| Polyoxyethylene (14) polyoxypropylene (7) dimethyl ether | 0.3 |
| Stearic acid | 3 |
| Palmitic acid | 1 |
| Myristic acid | 1 |
| Dimethicone | 5 |
| Zinc oxide | 3 |
| Sodium hydroxide | 0.3 |
| Phenoxyethanol | 0.5 |
| Hydroxypropyl methylcellulose stearoxy ether | 0.3 |
| Dimethylacrylamide/sodium acryloyldimethyl taurate crosspolymer | 0.2 |
| Total | 100 |

Polyoxypropylene glycol (*) = PPG1000 (molecular weight 1000)

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An oil-in-water emulsion sunscreen cosmetic comprising:
    (A) 5 to 40 mass % of one or more UV protective agents selected from the group consisting of UV absorbing agents and UV scattering agents;
    (B) 5 to 20 mass % of a linear higher fatty acid that is solid at room temperature and that has 8 to 22 carbon atoms; and
    (C) 0.1 to 5 mass % of one or more oils having at least an 0.5 IOB, wherein the one or more oils are ester oils, or are selected from the group consisting of polyethylene glycols, polypropylene glycols, polybutylene glycols, polyoxybutylene polyoxypropylene glycols, polyoxyethylene polyoxypropylene glycols and random polyoxyethylene/polyoxypropylene dimethyl ethers;
    wherein a neutralization rate of the fatty acid is 13% to 51%;
    wherein a blending ratio (A)/(B), between the (A) UV protective agent and the (B) fatty acid that is solid at room temperature ranges from 0.1 to 4.1;
    wherein the UV protective effect of the cosmetic is improved upon coming into contact with moisture; and wherein the cosmetic does not comprise a surfactant.

2. The cosmetic according to claim 1 wherein:
    the (C) oil is at least one selected from the group consisting of random polyoxyethylene/polyoxypropylene dimethyl ethers polyethylene, glycol, polypropylene glycol, polybutylene glycol, polyoxybutylene polyoxypropylene glycol and polyoxyethylene polyoxypropylene glycol.

3. The cosmetic according to claim 1, wherein:
    the (C) oil is at least one selected from the group consisting of random polyoxyethylene (14) polyoxypropylene (7) dimethyl ether, polyethylene glycol, polypropylene glycol, and polyoxybutylene polyoxypropylene glycol.

4. The cosmetic according to claim 1, wherein:
    the (B) linear higher fatty acid is one or more linear hi her fatty acids selected from the group consisting of stearic acid, palmitic acid, myristic acid, and behenic acid.

5. The cosmetic according to claim 1, wherein:
    the (C) oil is one or more selected from the group consisting of
    alkylene polyglycol dineopentanoate, random polyoxyethylene (14) polyoxypropylene (7) dimethyl ether, polyoxybutylene (9) polyoxypropylene (1) glycol, polypropylene glycol, polyethylene glycol having molecular weight 400, and polyethylene glycol having molecular weight 20000.

6. The cosmetic according to claim 1, wherein:
    the (A) UV protective agent is one or more selected from the group consisting of ethylhexyl methoxycinnamate, octocrylene, polysilicone-15, diethylamino hydroxybenzoyl hexyl benzoate, bis-ethylhexyloxyphenol methoxyphenyl triazine, zinc oxide, and titanium oxide.

7. An oil-in-water emulsion sunscreen cosmetic comprising:
    (A) 5 to 40 mass % of one or more UV protective agents selected from the group consisting of UV absorbing agents and UV scattering agents;
    (B) 5 to 20 mass % of a linear higher fatty acid that is solid at room temperature and that has 8 to 22 carbon atoms; and
    (C) 0.1 to 5 mass % of one or more oils having at least an 0.5 IOB, wherein the one or more oils are ester oils, or are selected from the group consisting of polyethylene glycols, polypropylene glycols, polybutylene glycols, polyoxybutylene polyoxypropylene glycols, polyoxyethylene polyoxypropylene glycols and random polyoxyethylene/polyoxypropylene dimethyl ethers;
    wherein a neutralization rate of the fatty acid is 13% to 51%;
    wherein a blending ratio (A)/(B), between the (A) UV protective agent and the (B) fatty acid that is solid at room temperature ranges from 0.1 to 4.1;
    wherein the UV protective effect of the cosmetic is improved upon coming into contact with moisture; wherein the cosmetic does not comprise a surfactant;
    wherein the (A) UV absorbing agents and UV scattering agents are one or more selected from the group consisting of ethylhexyl methoxycinnamate, octocrylene, polysilicone-15, diethylamino hydroxybenzoyl hexyl benzoate, bis-ethylhexyloxyphenol methoxyphenyl triazine, zinc oxide, and titanium oxide;
    wherein the (B) linear higher fatty acid is one or more linear hi her fatty acids selected from the group consisting of stearic acid, palmitic acid, myristic acid, and behenic acid; and
    wherein the (C) ester oils, polyethylene glycols, polypropylene glycols, polybutylene glycols, polyoxybutylene polyoxypropylene glycols, polyoxyethylene polyoxypropylene glycols and random polyoxyethylene/polyoxypropylene dimethyl ethers are selected from the group consisting of alkylene polyglycol dineopentanoate, random polyoxyethylene (14) polyoxypropylene (7) dimethyl ether, polyoxybutylene (9) polyoxypropylene (1) glycol, polypropylene glycol, polyethylene glycol having molecular weight 400, and polyethylene glycol having molecular weight 20000.

* * * * *